(12) United States Patent
Chen et al.

(10) Patent No.: US 9,052,269 B1
(45) Date of Patent: Jun. 9, 2015

(54) METHODS FOR CHARACTERIZING RELATIVE FILM DENSITY USING SPECTROSCOPIC ANALYSIS AT THE DEVICE LEVEL

(75) Inventors: Lifan Chen, Fremont, CA (US); Haifeng Wang, Morgan Hill, CA (US); Li Zeng, Fremont, CA (US); Dehua Han, Fremont, CA (US)

(73) Assignee: Western Digital (Fremont), LLC., Fremont, CA (US)

( * ) Notice: Subject to any disclaimer, the term of this patent is extended or adjusted under 35 U.S.C. 154(b) by 513 days.

(21) Appl. No.: 13/460,501

(22) Filed: Apr. 30, 2012

(51) Int. Cl.
G06F 19/00 (2011.01)
G01N 31/00 (2006.01)
G01N 23/083 (2006.01)

(52) U.S. Cl.
CPC .................... G01N 23/083 (2013.01)

(58) Field of Classification Search
CPC .............. G01N 9/36; G01N 2223/601; G01N 2223/633; G01N 2223/0563; G01N 2223/206; G01N 2223/424; G01N 2291/0218; G01N 23/20091; G01N 23/083
USPC ......... 702/28, 40, 49, 134, 137, 156, 172, 27; 427/569; 438/14
See application file for complete search history.

(56) References Cited

U.S. PATENT DOCUMENTS 7,595,204 B2 * 9/2009 Price ............................... 438/14
8,025,932 B2 * 9/2011 Wolden et al. ................ 427/569

OTHER PUBLICATIONS

R.F. Egerton, "Electron Energy-Loss Spectroscopy in the Electron Microscope", Publication Date: Jul. 29, 2011, Publisher: Springer, 3rd ed., pp. 135-169.

* cited by examiner

Primary Examiner — John H Le

(57) ABSTRACT

Methods for characterizing relative film density using spectroscopic analysis at the device level are provided. One such method includes obtaining a composition of materials at preselected areas of a workpiece using energy dispersive X-ray spectroscopy, obtaining an electron energy loss spectrum-imaging data at each of the preselected areas using electron energy loss spectroscopy, removing, for each of the preselected areas, a preselected noise component of the electron energy spectrum-imaging data to form a plasmon energy spectrum-imaging data, generating, for each of the preselected areas, a plasmon energy map based on the respective plasmon energy spectrum-imaging data, determining, for each of the preselected areas, an average plasmon energy value from the respective plasmon energy map, and calculating a relative mass density of the preselected areas based on the average plasmon energy value, a number of valence electrons per molecule, and a molecular weight for each of the preselected areas.

11 Claims, 2 Drawing Sheets

METHODS FOR CHARACTERIZING RELATIVE FILM DENSITY USING SPECTROSCOPIC ANALYSIS AT THE DEVICE LEVEL

FIELD

The present invention relates generally to processes or methods for determining mass density, and more specifically to methods for characterizing relative film density using spectroscopic analysis at the device level.

BACKGROUND

Commonly used methods for characterizing mass density of thin films include X-ray reflectivity (XRR) and Rutherford backscattering (RBS). However, there are limitations for both the XRR and RBS methods related to large probe size and sample volume. As such, these methods work well only on full film samples and cannot be used to probe localized device structures of a nanometer scale, such as magnetic writer head devices with complicated topography and nanometer scale sized areas of interest thereon.

Another method, X-ray diffraction (XRD), can probe thin film structure and measure the lattice constant and therefore deduce the mass density if the film composition is known. However, similar to the XRR method which uses X-ray as the probe beam, it is generally impossible to utilize at the nanometer scale for current writer devices. As such, a method for characterizing film density at the nanometer scale device level that addresses these shortcomings is needed.

SUMMARY

Aspects of the invention relate to methods for characterizing relative film density using spectroscopic analysis at the device level. In one embodiment, the invention relates to a method for characterizing relative film density at the device level, the method including obtaining a composition of materials at a plurality of preselected areas of a workpiece using energy dispersive X-ray spectroscopy, determining, by a processor, a molecular weight and a number of valence electrons per molecule for each of the plurality of preselected areas based on the composition of materials, obtaining an electron energy loss spectrum-imaging data at each of the plurality of preselected areas using electron energy loss spectroscopy, removing, by the processor and for each of the plurality of preselected areas, a preselected noise component of the electron energy loss spectrum-imaging data to form a plasmon energy spectrum-imaging data, generating, by the processor and for each of the plurality of preselected areas, a plasmon energy map based on the respective plasmon energy spectrum-imaging data, determining, by the processor and for each of the plurality of preselected areas, an average plasmon energy value from the respective plasmon energy map, and calculating, by the processor, a relative mass density of the plurality of preselected areas based on the average plasmon energy value, the number of valence electrons per molecule, and the molecular weight for each of the plurality of preselected areas.

DETAILED DESCRIPTION

Figure 1:
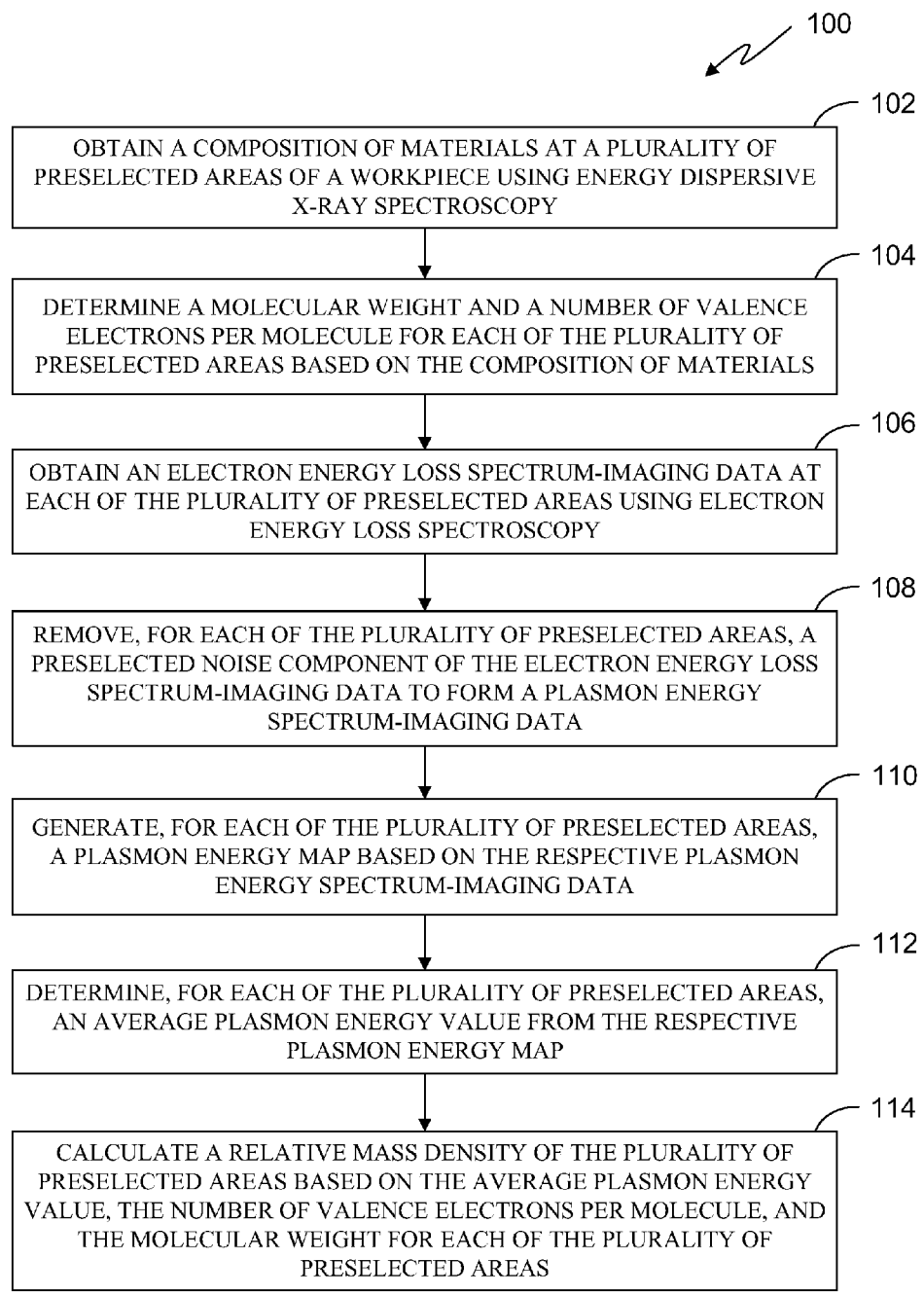
FIG. 1 is a flowchart of a process for characterizing relative film mass density using spectroscopic analysis at the nanoscale device level in accordance with one embodiment of the invention.

Referring now to the drawings, embodiments of methods for characterizing relative film density using spectroscopic analysis at the device level are illustrated. The state-of-the-art electron energy loss spectroscopy (EELS) setup combined with scanning transmission electron microscope (STEM) imaging and energy dispersive X-ray spectroscopy (EDS) composition analysis enables the characterization of film density on transmission electron microscope (TEM) device samples with nanometer scale sample size. With these tools, a process for determining the relative mass density of two or more preselected areas on a nanometer scale workpiece that is based on the use of EELS and EDS along with application of the Drude model equation for free electron plasmon energy has been developed and is described in detail below.

While not bound by any particular theory, this new characterization methodology can be important to current and future magnetic head development and production. With the continued scaling down of the magnetic head, large on-track write field gradient for better magnetic signal to noise ratio (SNR) is needed for the future generations of magnetic heads. To achieve this requirement, writer geometry often becomes quite complicated. The resulting complex topography imposes big challenges on thin film deposition, including undesirable shadowing effects imposed on film density. An important challenge for such topographies is how to characterize the density loss on the bevel of the writer. The methods for characterizing relative film density using spectroscopic analysis described herein provide versatile and unique ways to characterize the mass density of multilayer thin films for not only full film level, but importantly also for devices at the wafer level. In several embodiments, a method for characterizing relative film density using spectroscopic analysis can be applied as long as a TEM sample can be prepared, which is almost always feasible.

FIG. 1 is a flowchart of a process 100 for characterizing relative film mass density using spectroscopic analysis at the nanoscale device level in accordance with one embodiment of the invention. The process first obtains (102) a composition of materials at two or more preselected areas of a workpiece using energy dispersive X-ray spectroscopy (EDS). In several embodiments, one of the preselected areas is a substantially flat area which can be used as a reference or baseline area. In a number of embodiments, the EDS is performed using a suitable scanning transmission electron microscope. The process then determines (104) a molecular weight and a number of valence electrons per molecule for each of the preselected areas based on the composition of materials. The process obtains (106) an electron energy loss spectrum-imaging data at each of the preselected areas using electron energy loss spectroscopy (EELS).

The process then removes (108), for each of the preselected areas, a preselected noise component of the electron energy loss spectrum-imaging data to form a plasmon energy spectrum-imaging data. In several embodiments, the preselected noise component is a plural scattering noise component or other undesirable artifact. In such case, removing the plural scattering noise component can substantially eliminate any effects associated with differences in the relative thicknesses of the preselected areas. In a number of embodiments, the process removes the preselected noise component using a Fourier log or Fourier ratio sub-process. The process generates (110), for each of the preselected areas, a plasmon energy map based on the respective plasmon energy spectrum-imaging data. In a number of embodiments, the plasmon energy map for each of the preselected areas is generated using a non-linear least squares fitting of a Gaussian function, a Lorentz function, or another suitable function.

The process then determines (112), for each of the preselected areas, an average plasmon energy value from the respective plasmon energy map. The process calculates (114) a relative mass density of the preselected areas based on the average plasmon energy value, the number of valence electrons per molecule, and the molecular weight for each of the preselected areas. In several embodiments, the calculation is performed using a Drude model equation. The Drude model equation can be derived from quantum theory, and more specifically, the plasmon energy equation, which is given by:

$$Ep = \hbar \omega_P = \hbar * \left(\frac{ne^2}{\varepsilon_0 m}\right)^{1/2}$$

where h is Planck's constant, e is the electron charge, m is the effective mass, $\varepsilon_0$ is the permittivity of vacuum, and n is the free valence electron density. In the Drude theory of electrical conduction in metals, taking $m=m_0$ ($m_0$ is the rest mass of an electron) and writing electron density as $n=(z\rho)/(uA)$ where z is the number of free (valence) electrons per atom, u is the atomic mass unit, A represents atomic weight, and $\rho$ is the mass density (g/cm$^3$) of the solid, the free electron plasmon energy (e.g., average plasmon energy value) is conveniently evaluated as:

$$Ep = (28.82 \text{ eV}) * \left(\frac{z\rho}{A}\right)^{1/2}$$

where eV is electron volts, z is the number of valence electrons per molecule, A is the molecular weight, and $\rho$ is the relative mass density. Once the average plasmon energy value Ep, z, and A are known, as are determined in blocks 104 and 112 of the process, then the relative mass density $\rho$ can easily be determined from this equation in block 114.

In one embodiment, the process can perform the sequence of actions in a different order. In another embodiment, the process can skip one or more of the actions. In other embodiments, one or more of the actions are performed simultaneously. In some embodiments, additional actions can be performed.

In several embodiments, the results of the relative mass density determination are used as a guide for process development, optimization, and improvement of development cycle time for magnetic head development and production. The process can be carried out with routine analytical TEM imaging and analysis. The results are generally comparable and repeatable. The new method can detect as low as 2 percent reduction in mass density when there are no visible voids and cracks from regular TEM and STEM imaging. In some cases, the new method has confirmed that density difference can be as large as 6 to 7 percent between a flat region and a sloped region with a bevel angle of about 65 degrees for a portion of a magnetic head. This discovery can lead to rapid process improvement decisions without waiting for backend data confirmation, thereby shortening development cycles significantly.

Figure 2:
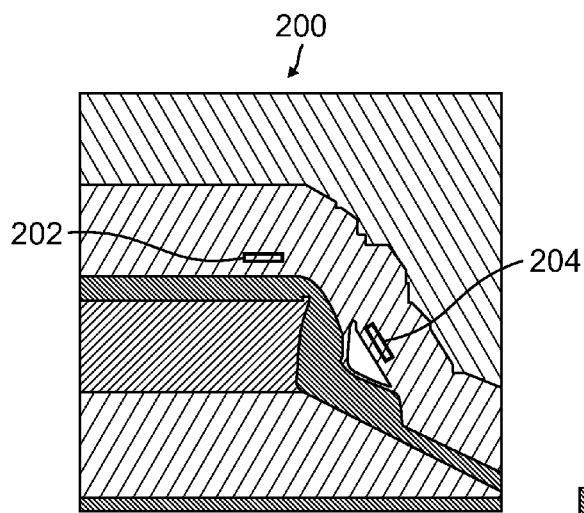
FIG. 2 is a cross sectional view of a nanoscale device structure including CoFe materials and formed using ion beam etching to have flat areas and sloped areas that have been probed with a scanning transmission electron microscope (STEM) using the process of FIG. 1 to characterize the relative film mass density in accordance with one embodiment of the invention.

FIG. 2 is a cross sectional view of a nanoscale device structure 200 including CoFe materials and formed using ion beam etching to have flat areas 202 and sloped areas 204 that have been probed with a scanning transmission electron microscope (STEM) using the process of FIG. 1 to characterize the relative film mass density in accordance with one embodiment of the invention. The probe results show no visible defects in the STEM data and about 2 percent mass density reduction at the sloped area 204 (e.g., about 60 degrees bevel) as compared to the flat area 202.

Figure 3:
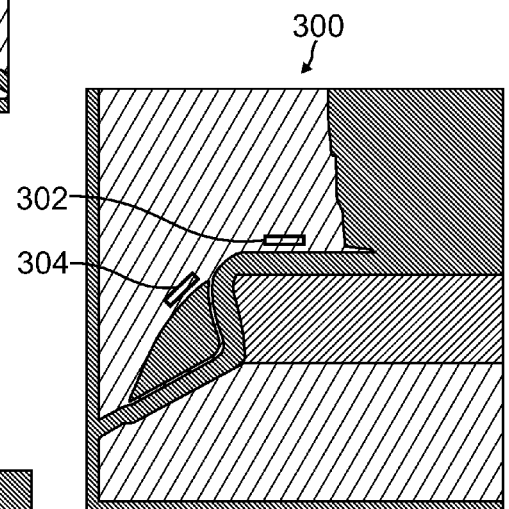
FIG. 3 is a cross sectional view of a nanoscale device structure including CoNiFe materials and formed using reactive ion etching to have flat areas and sloped areas that were probed with the scanning transmission electron microscope (STEM) using the process of FIG. 1 to characterize the relative film mass density in accordance with one embodiment of the invention.

FIG. 3 is a cross sectional view of a nanoscale device structure 300 including CoNiFe materials and formed using reactive ion etching to have flat areas 302 and sloped areas 304 that were probed with the scanning transmission electron microscope (STEM) using the process of FIG. 1 to characterize the relative film mass density in accordance with one embodiment of the invention. The probe results show no visible defects in the STEM data and about 3 percent mass density reduction at the sloped area 304 (e.g., about 40 degrees bevel) as compared to the flat area 302.

Figure 4:
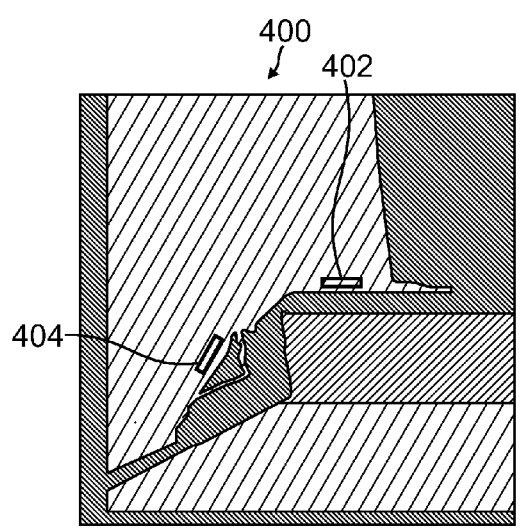
FIG. 4 is a cross sectional view of a nanoscale device structure including CoNiFe materials and formed using ion beam etching to have flat areas and sloped areas that have been probed with the scanning transmission electron microscope (STEM) using the process of FIG. 1 to characterize the relative film mass density in accordance with one embodiment of the invention.

FIG. 4 is a cross sectional view of a nanoscale device structure 400 including CoNiFe materials and formed using ion beam etching to have flat areas 402 and sloped areas 404 that have been probed with the scanning transmission electron microscope (STEM) using the process of FIG. 1 to characterize the relative film mass density in accordance with one embodiment of the invention. The probe results show no visible defects in the STEM data and about 6 percent mass density reduction at the sloped area 404 (e.g., about 60 degrees bevel) as compared to the flat area 402.

While the above description contains many specific embodiments of the invention, these should not be construed as limitations on the scope of the invention, but rather as examples of specific embodiments thereof. Accordingly, the scope of the invention should be determined not by the embodiments illustrated, but by the appended claims and their equivalents.

What is claimed is:

1. A method for characterizing relative film density at a device level, the method comprising:
    obtaining a composition of materials at a plurality of preselected areas of a workpiece using energy dispersive X-ray spectroscopy;
    determining, by a processor, a molecular weight and a number of valence electrons per molecule for each of the plurality of preselected areas based on the composition of materials;
    obtaining an electron energy loss spectrum-imaging data at each of the plurality of preselected areas using electron energy loss spectroscopy;

removing, by the processor and for each of the plurality of preselected areas, a preselected noise component of the electron energy loss spectrum-imaging data to form a plasmon energy spectrum-imaging data;

generating, by the processor and for each of the plurality of preselected areas, a plasmon energy map based on the respective plasmon energy spectrum-imaging data;

determining, by the processor and for each of the plurality of preselected areas, an average plasmon energy value from the respective plasmon energy map; and calculating, by the processor, a relative mass density of the plurality of preselected areas based on the average plasmon energy value, the number of valence electrons per molecule, and the molecular weight for each of the plurality of preselected areas.

2. The method of claim 1, wherein one of the plurality of preselected areas of the workpiece is used as a reference in calculating the relative mass density.

3. The method of claim 1, wherein the removing, by the processor and for each of the plurality of preselected areas, the preselected noise component of the electron energy loss spectrum-imaging data to form the plasmon energy spectrum-imaging data comprises removing a plural scattering in the electron energy loss spectrum-imaging data for each of the respective plurality of preselected areas.

4. The method of claim 3, wherein the removing the plural scattering in the electron energy loss spectrum-imaging data comprises performing a sub-process selected from the group consisting of a Fourier log sub-process and a Fourier ratio sub-process.

5. The method of claim 3, wherein the removing the plural scattering in the electron energy loss spectrum-imaging data substantially eliminates a thickness effect associated with the plurality of preselected areas.

6. The method of claim 1, wherein the generating, by the processor and for each of the plurality of preselected areas, the respective plasmon energy map based on the plasmon energy spectrum-imaging data comprises generating, for each of the plurality of preselected areas, the respective plasmon energy map based on the plasmon energy spectrum-imaging data using a non-linear least squares fitting.

7. The method of claim 1, wherein the generating, by the processor and for each of the plurality of preselected areas, the plasmon energy map based on the respective plasmon energy spectrum-imaging data comprises generating, for each of the plurality of preselected areas, the plasmon energy map based on the respective plasmon energy spectrum-imaging data using a non-linear least squares fitting of a preselected function selected from the group consisting of a Gaussian function and a Lorentz function.

8. The method of claim 1, wherein the calculating, by the processor, the relative mass density of the plurality of preselected areas based on the average plasmon energy value, the number of valence electrons per molecule, and the molecular weight for each of the plurality of preselected areas comprises using a Drude model equation.

9. The method of claim 8, wherein the Drude model equation is:

$$Ep = (28.82 \text{ eV}) * \left(\frac{z\rho}{A}\right)^{1/2}$$

wherein Ep is the average plasmon energy value, eV is electron volts, z is the number of valence electrons per molecule, A is the molecular weight, and $\rho$ is the relative mass density.

10. The method of claim 1, wherein each of the plurality of preselected areas comprises an area selected from the group consisting of a sloped surface, a flat surface, and combinations thereof.

11. The method of claim 1, further comprising modifying a manufacturing characteristic of a magnetic thin film workpiece based on the calculated relative mass density.

* * * * *